(12) United States Patent
Matusch

(10) Patent No.: US 8,545,441 B2
(45) Date of Patent: Oct. 1, 2013

(54) INJECTOR HAVING A DISPLACEABLE STOPPER PART

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 266 days.

(21) Appl. No.: 13/135,428

(22) Filed: Jul. 5, 2011

(65) Prior Publication Data

US 2011/0270167 A1 Nov. 3, 2011

Related U.S. Application Data

(63) Continuation-in-part of application No. PCT/EP2010/000031, filed on Jan. 7, 2010.

(30) Foreign Application Priority Data

Jan. 13, 2009 (DE) .......................... 10 2009 004 828

(51) Int. Cl.
| | |
|---|---|
| *A61M 5/00* | (2006.01) |
| *A61M 37/00* | (2006.01) |
| *B67C 3/00* | (2006.01) |
| *B65B 1/04* | (2006.01) |
| *B65B 3/04* | (2006.01) |

(52) U.S. Cl.
USPC ............... 604/89; 604/232; 141/18; 141/330; 141/346

(58) Field of Classification Search
USPC ................. 604/68, 71, 82–92, 232, 403, 407; 141/18, 330, 329, 346
See application file for complete search history.

(56) References Cited

U.S. PATENT DOCUMENTS

| | | | | |
|---|---|---|---|---|
| 3,610,297 | A | | 10/1971 | Raaf |
| 3,946,732 | A | * | 3/1976 | Hurscham ........................ 604/88 |
| 4,994,029 | A | * | 2/1991 | Rohrbough ..................... 604/88 |
| 5,045,067 | A | | 9/1991 | Ohnaka et al. |
| 6,645,171 | B1 | * | 11/2003 | Robinson et al. ............... 604/82 |
| 6,673,035 | B1 | * | 1/2004 | Rice et al. ........................ 604/72 |
| 7,341,575 | B2 | * | 3/2008 | Rice et al. ..................... 604/232 |

(Continued)

FOREIGN PATENT DOCUMENTS

| | | |
|---|---|---|
| DE | 6607420 U | 2/1971 |
| DE | 75 23 544 U | 1/1976 |
| DE | 75 235 44 U | 1/1976 |
| DE | 36 18 158 A1 | 12/1987 |
| EP | 0 904 763 A2 | 3/1999 |

(Continued)

*Primary Examiner* — Matthew F Desanto
(74) *Attorney, Agent, or Firm* — R. S. Lombard; K. Bach

(57) ABSTRACT

A disposable injector (4) having a two-chamber system (99), wherein at least one first chamber (105) is part of a piston-cylinder unit (100) that can be accommodated in the disposable injector (4), and wherein the second chamber (255) is part of a chamber (250) which is at least temporarily closed by means of a stopper (257) and inserted into a container adapter (200) detachably mounted on the disposable injector (4), or part of a piston-cylinder unit (254), and wherein the container adapter (200) comprises a connecting tube (242) initially closed by means of a cap (290). To this end, on the side oriented toward the second chamber, the stopper has a recess (271), into which at least one stopper channel (275) connecting the lateral surface (277) of the stopper to the recess (271) opens. After the container has been pushed in or activated, the connecting tube (242) connects the interior of the piston-cylinder unit to the interior of the container or of the piston-cylinder unit via the stopper channel and the tubular channel.

14 Claims, 6 Drawing Sheets

(56) References Cited

U.S. PATENT DOCUMENTS

| | | | |
|---|---|---|---|
| 7,744,563 B2 * | 6/2010 | Landau et al. | 604/68 |
| 7,963,954 B2 * | 6/2011 | Kavazov | 604/403 |
| 2009/0204066 A1 * | 8/2009 | Radmer et al. | 604/86 |
| 2010/0262125 A1 | 10/2010 | Matusch | |
| 2011/0152758 A1 | 6/2011 | Matusch | |

FOREIGN PATENT DOCUMENTS

| | | |
|---|---|---|
| FR | 2 894 463 A1 | 6/2007 |
| WO | WO 98/26819 | 6/1998 |
| WO | WO 00 15281 A1 | 3/2000 |
| WO | WO 01 87385 A1 | 11/2001 |
| WO | WO 2009 097966 A1 | 8/2009 |

* cited by examiner

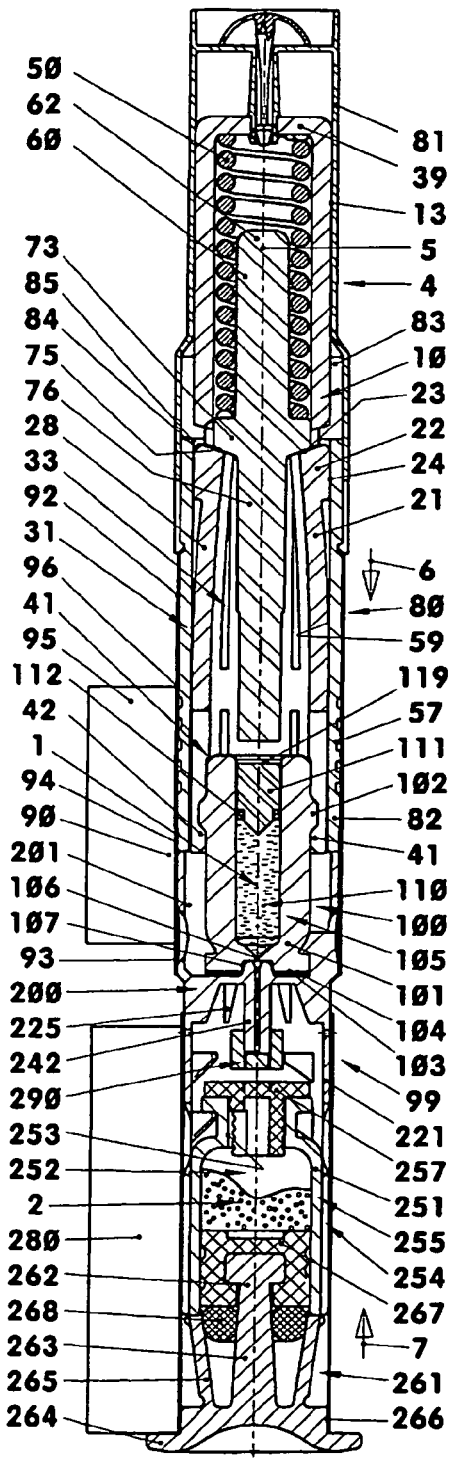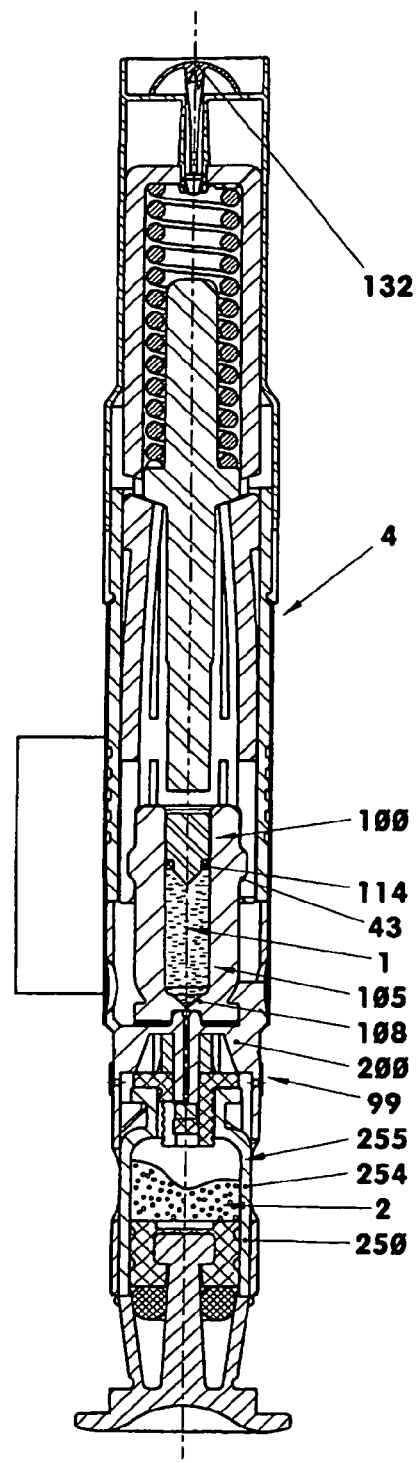

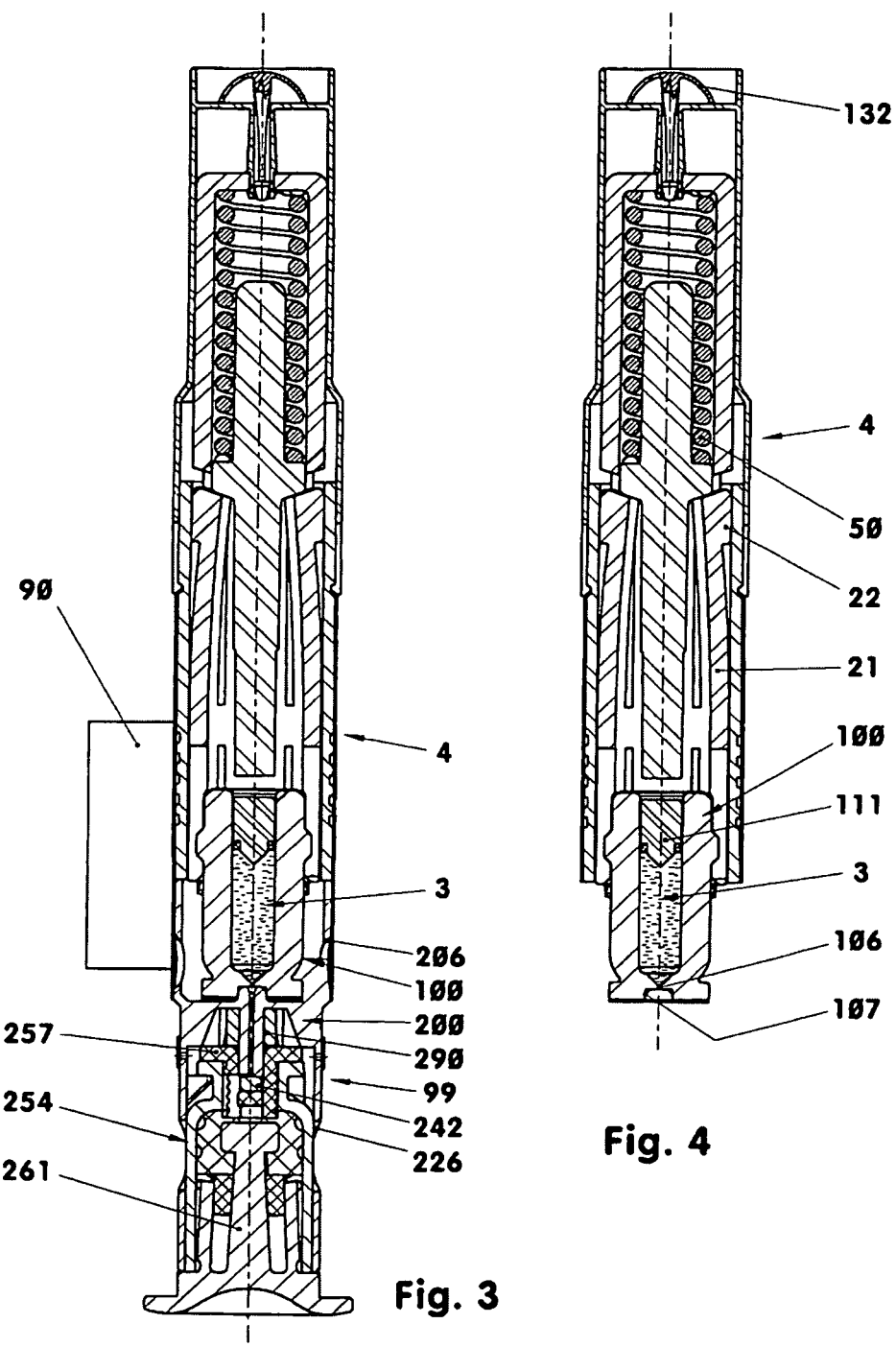

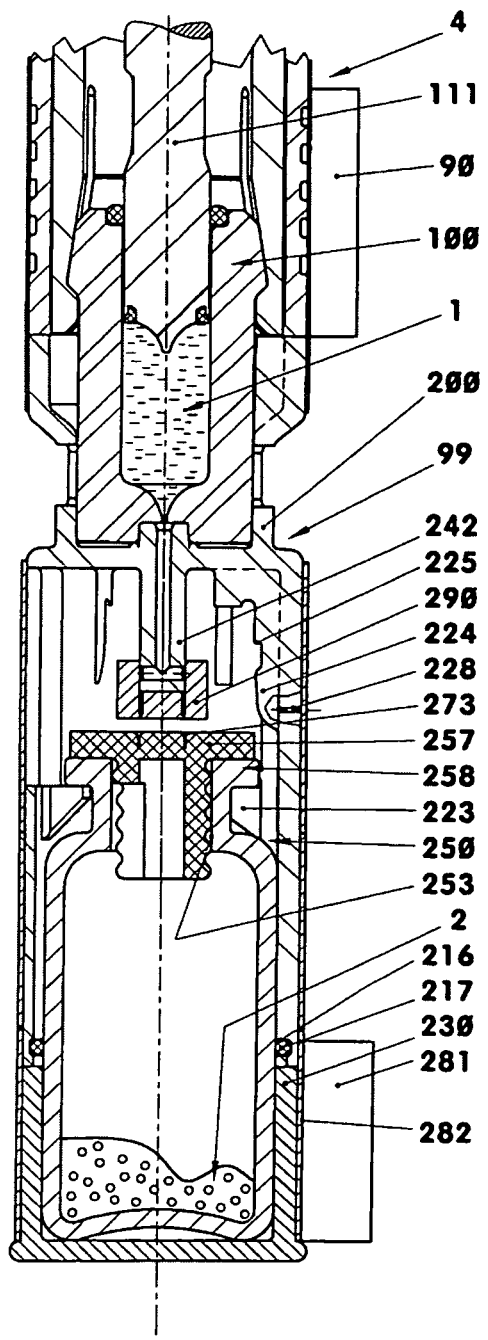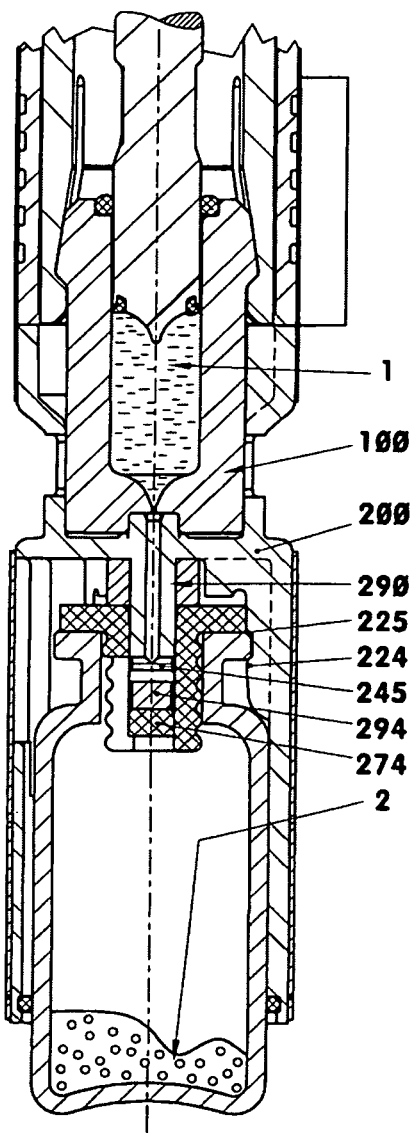
Fig. 8
Fig. 9

INJECTOR HAVING A DISPLACEABLE STOPPER PART

CROSS-REFERENCE TO RELATED APPLICATION

This is a continuation-in-part application of pending international application PCT/EP2010/000031 filed Jan. 7, 2010 and claiming the priority of German Application No. 10 2009 004 828.6 filed Jan. 13, 2009.

BACKGROUND OF THE INVENTION

The invention relates to a disposable injector having a twin-chamber system, wherein at least one first chamber is part of a sterile and gastight cylinder-piston unit which can be received in the disposable injector and wherein the second chamber is part of a container which is at least temporarily closed in a sterile and gastight manner by means of a stopper and inserted into a container adapter detachably mounted on the disposable injector, or part of a cylinder-piston unit, and wherein the container adapter comprises a connecting tube initially closed by means of a cap and having at least one tubular channel connecting a longitudinal bore to the lateral surface.

A disposable injector is known from DE 10 2008 003 105. The sterile closure of the first chamber is opened before insertion and is closed by means of a sealing nub. A dual adapter, inserted into the container adapter, pushes the stopper out of the opening, so that the stopper falls into the container. This may hinder the preparation of the injection solution.

The present invention is therefore based on the problem of preventing the falling of the stopper into the container. Furthermore, it is intended that both chambers can be individually stored, while closed in a sterile and gastight manner, until immediately before use.

SUMMARY OF THE INVENTION

The present invention provides a disposable injector (4) having a two-chamber system (99), wherein at least one first chamber (105) is part of a piston-cylinder unit (100) that can be accommodated in the disposable injector (4), and wherein the second chamber (255) is part of a chamber (250) which is at least temporarily closed by means of a stopper (257) and inserted into a container adapter (200) detachably mounted on the disposable injector (4), or part of a piston-cylinder unit (254), and wherein the container adapter (200) comprises a connecting tube (242) initially closed by means of a cap (290). To this end, on the side oriented toward the second chamber, the stopper has a recess (271), into which at least one stopper channel (275) connecting the lateral surface (277) of the stopper to the recess (271) opens. After the container has been pushed in or activated, the connecting tube (242) connects the interior of the piston-cylinder unit to the interior of the container or of the piston-cylinder unit via the stopper channel and the tubular channel. With the present invention, the stopper is prevented from falling in the container. In addition, both chambers can be stored individually, closed in a sterile and gas tight manner, until immediately before use.

BRIEF DESCRIPTION OF THE DRAWINGS

Further details of the invention will become clear from the following description of illustrative embodiments represented schematically in the drawing, in which:

FIG. 1 shows a disposable injector with a twin-chamber system comprising two cylinder-piston units;
FIG. 2 shows the disposable injector after the pushing-in of the second cylinder-piston unit;
FIG. 3 shows the disposable injector after the transfer-pumping;
FIG. 4 shows the disposable injector before the triggering;
FIG. 8 shows a detail of a disposable injector and a twin-chamber system with only one cylinder-piston unit and a container;
FIG. 9 shows FIG. 8 with a pushed-in container.

DETAILED DESCRIPTION OF THE PARTICULAR EMBODIMENTS

Figure 5:
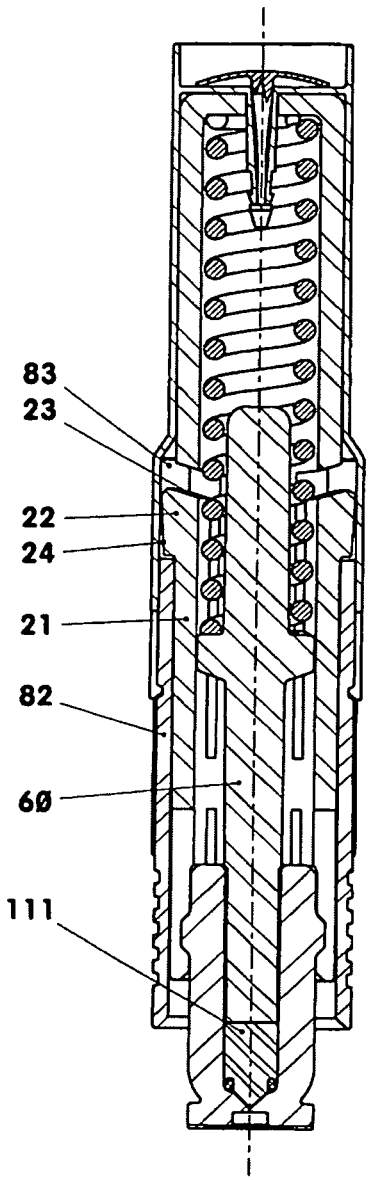
FIG. 5 shows FIG. 4 after the injection.

FIGS. 1-5 show a disposable injector (4) having a twin-chamber system (99) adapted to it. FIG. 1 shows, for example, the state on delivery to the user, in which the disposable injector (4) is pretensioned, the first chamber (105) is, for example, partially filled with solvent (1) and the second chamber (255) is, for example, partially filled with lyophilisate (2) and the two chambers (105, 255) are closed and separated from each other in a gastight and sterile manner. In the illustration of FIG. 2, the two chambers (105, 255) have been connected to each other for the preparation of an injection solution (3). FIG. 3 shows the disposable injector (4) and the twin-chamber system (99) after the preparation of the injection solution (3) and the transfer-pumping thereof into the injector-side chamber (105). FIG. 4 shows this injector (4) with the injector-side chamber (105) before the triggering. In the illustration of FIG. 5, the needleless disposable injector (4) has been triggered and the injection solution (3) injected out.

The disposable injector (4) illustrated in FIGS. 1-5 comprises a housing (10), a piston-actuating ram (60) and a helical compression spring (50) as a spring energy store. Moreover, a triggering unit (80) having a triggering element (82) and a security element (90) are arranged on the housing (10).

The housing 10 is a one-part, pot-shaped, downwardly open hollow body with a base (39) at the top. It is produced, for example, from a glassfiber-reinforced polyamide by injection molding. The housing (10) has a largely tubular shape and is divided into two functional areas, on the one hand the upper lateral area (31) and on the other hand the lower fixing area (41).

In the lateral area (31), the housing (10) has, for example, two mutually opposite window-like apertures (33). On the lower edge of the individual aperture (33), a pressure rod (21) is in each case integrally formed as an elastic flexural beam. The location where the pressure rods (21) are integrally formed lies just above the fixing area (41). For the formation of the respective pressure rod (21), there is in the lower area of the lateral portion (31) a narrow, at least approximately u-shaped gap, which surrounds the individual pressure rod (21) to the sides and on top.

Along 80% of its length, for example, the pressure rod (21) has the wall thickness and curvature of the wall of the housing (10). This area also has the function, inter alia, of a resiliently elastic flexural beam (28). It has, for example, a crescent-shaped cross section.

In the case of injectors in which the piston-actuating ram (60) is guided straight with little play in the housing (10)—at least in some portions—and the piston-actuating ram (60) has sufficient flexural strength, just a single pressure rod (21) may be used instead of two or more pressure rods (21).

The free end of the individual pressure rod (21), here the upper end, is formed by the radially outwardly protruding cam (22). The latter has at least one supporting surface (23), oriented in the direction of the center line (5), and a bearing surface (24), facing away from the center line (5).

The lower half of the housing (10) is surrounded by the sleeve-like triggering element (82). This is, for example, of a substantially cylindrical form and is produced, for example, from acrylonitrile-butadiene-styrene copolymer (ABS). The triggering element (82) is mounted so as to be movable along the radial outer surface (13) of the housing (10). It ends at the rear with a sharp edge (85), which is part of a return flank (84) at the end face of the triggering element (82). Below the edge (85), according to FIG. 1, the cams (22) formed integrally on the pressure rods (21) make secure contact with the inner wall (59) of the triggering element (82) with their outer bearing surfaces (24).

A triggering cap (81), which completely surrounds the rear end of the housing (10), is secured on the triggering element (82), for example near the edge (85). The triggering cap (81) comprises a circumferential widening (83), in which the cams (22) are received when the injector is triggered, cf. FIG. 5. Instead of this widening (83), partial widenings or uncovered openings may also be provided for each pressure rod (21) in the case of a non-rotationally symmetrical triggering element (82). Above the widening (83), the triggering cap (81) bears slidably on the outer wall (13) of the housing (10).

The piston-actuating ram (60) arranged in the housing (10) is divided into two areas. The lower area is the piston slide (76). The diameter thereof is slightly smaller than the inside diameter of the rear area of the cylinder (101) of a cylinder-piston unit (100). The lower end face of the piston slide (76) acts directly on the piston (111) of this cylinder-piston unit (100).

The upper area of the piston-actuating ram (60), the ram plate (73), is a flat, at last partially cylindrical disk, of which the outside diameter is several tenths of a millimeter smaller than the inside diameter of the housing (10) in the lateral area (31). The lower end face has a collar surface (75) arranged around the piston slide (76). It has the form of the lateral surface of a truncated cone of which the vertex angle is about 100 to 140 degrees. The imaginary vertex of the lateral surface of the truncated cone lies on the center line (5) in the area of the piston slide (76). The collar surface (75) may also be spherically curved.

The piston slide (76) may of course also be designed as a component that is separate from the ram plate (73). For this purpose, it is then guided on the inner wall of the housing (10).

The helical compression spring (50) sits pretensioned between the ram plate (73) and the base (39) lying at the top of the housing (10). The helical compression spring (50) is supported on the base (39) of the housing (10). The spring force of the helical compression spring (50) is transferred to the pressure rods (21) by way of the ram plate (73). On account of the inclination of the collar surface (75), the pressure rods (21) are forced radially outward in the manner of a wedge gear. The triggering sleeve (82) permanently supports this radial force.

Above the ram plate (73), the piston-actuating ram (60) has a guide pin (62). The latter guides the helical compression spring (50) or is guided by the latter. Below the ram plate (73), the piston slide (76) is located centrally in the continuation of the guide pin (62).

The fixing area (41) for receiving the insertable cylinder-piston unit (100) comprising the first chamber (105) is located below the lateral portion (31). The fixing area (41) comprises, for example, eight spring hooks (42) oriented parallel to the center line (5). The spring hooks (42) each have an at least two-flanked rear-engagement means (43) for receiving the cylinder-piston unit (100) free of play. The mutually opposite flanks of the rear-engagement means (43) enclose an angle of 90 degrees, for example. The length and the spring rate of the spring hooks (42) are dimensioned such that the cylinder-piston unit (100) can be inserted without plastic deformation of the spring hooks (42).

In the illustrative embodiment, the cylinder-piston unit (100) is composed of a transparent cylinder (101), which can be filled with water for injection purposes (1) or an injection solution (3). The water for injection purposes (1) may already contain active substances. In the illustration of FIG. 1, the piston (111) is in the rear position. Above the piston (111), the piston-actuating ram (60) is arranged in the housing (10) in such a way, for example, that although not touching the piston (111) it is guided laterally with its lower end, for example, in the upper area of the cylinder (101).

The cylinder (101) is, for example, a see-through, thick-walled pot, of which the optionally cylindrical outer wall supports a, for example circumferential, locking ring (102) that bears in a dimensionally stable manner on the flanks of the rear-engagement means (43) of the spring hooks (42). The rodless piston (111) sits in the, for example cylindrical, bore of the cylinder (101). At its front, at least approximately conical end face, the piston (111) has an axial annular groove (112) for receiving a sealing ring (114) or a permanently elastic sealing compound. Optionally, a, for example cylindrical, metal plate is let into the rear end face of the piston (111).

A short cylindrical, nozzle-like bore (106) is located at the center of the bore of the cylinder (101), the cylinder base of which is at least approximately adapted to the contour of the front piston end face. The diameter of the nozzle-like bore is approximately 0.1 to 0.5 millimeter. This bore (106) is 1 to 5 times as long as its diameter. It ends in a cylindrical recess (107) of the base-side, outer end face (103) of the cylinder (101). In order to increase application safety, this end face (103) may be additionally provided with an adhesive ring (104).

The cylinder (101) is closed at the rear in a sterile manner by a sterile filter membrane (119).

Also inserted into the disposable injector (4) is a container adapter (200). This is a bushing-like component which receives, for example, the second chamber (255)—which is in FIGS. 1 to 3, 6 and 7 part of a container (250) of variable volume formed as a cylinder-piston unit (254)—in a container area (221). At the same time, said container adapter has a sleeve-shaped adapter area (201) with which it sits longitudinally movably in the housing (10).

The adapter area (201) is a cylindrical cup which surrounds at least the lower fifth of the cylinder (101) with a spacing. It has two mutually opposite, for example circular, windows (206) and an annular shoulder (204) on the intermediate base (211). The windows (206) may be omitted if the material of the container adapter is transparent.

Figure 6:
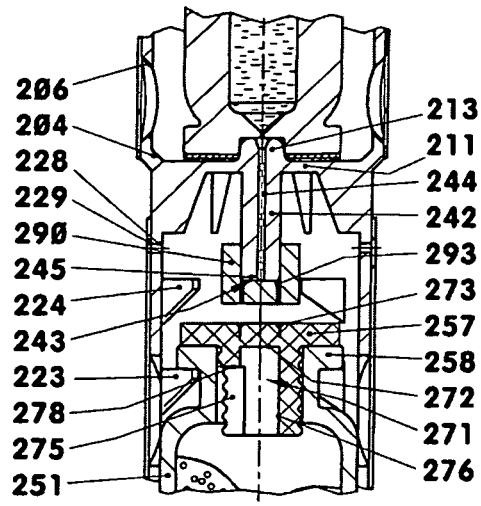
FIG. 6 shows a detail of FIG. 1.

A transfer tube (242), which connects the adapter area (201) and the container area (221) to each other, is arranged centrally in the intermediate base (211), cf. FIG. 6. For centering and for connecting in a sterile, sealing manner at the recess (107), the surface facing the adapter area (201) has a central elevation (213). The transfer tube (242) is, for example, cylindrical and has an outside diameter of, for example, four millimeters. In the illustrative embodiment, its length is four times the outside diameter and its minimum inside diameter, the diameter of the bore (244), corresponds to at least the diameter of the nozzle-like bore (106). The minimum diameter of the bore (244) may be, for example, one millimeter. For example, the diameter of the bore (244) may taper, for example conically, from both end faces toward the center or from one end face toward the other.

At its end face (243) pointing in the direction of the container (250), the transfer tube (242) has, for example, an at least approximately radially oriented channel (245), which connects the bore (244) to the lateral surface (247) of the transfer tube (242). At least approximately radial means here that the angular area in which the channel is arranged is bounded by tangents to the bore (244). The, for example flute-shaped, channel (245) has in the illustrative embodiment a constant cross-sectional area over its length, corresponding to half the cross-sectional area of the bore (244). The cross-sectional area of the tubular channel (245) may be greater; for example, it may correspond to the cross-sectional area of the bore (244). The depth of this flute-shaped tubular channel (245) corresponds here to the radius of the longitudinal bore (244). In the illustrative embodiment, the channel (245) opens out at the lateral surface (247) into a circumferential groove (248).

Figure 11:
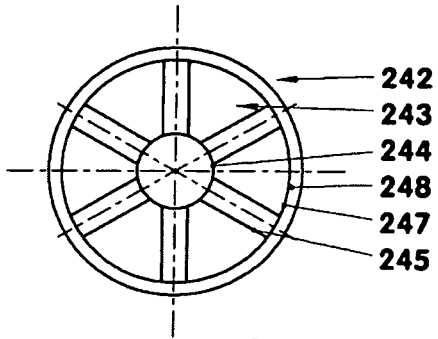
FIG. 11 shows the end face of a transfer tube.

FIG. 11 shows an end face (243) of a connecting tube (242) with six regularly arranged, radially oriented channels (245). Each of these channels (245) is constructed like the channel (245) shown in FIGS. 1-6. The channels (245) open out at the lateral surface (247) into a circumferential groove (248).

Figure 12:
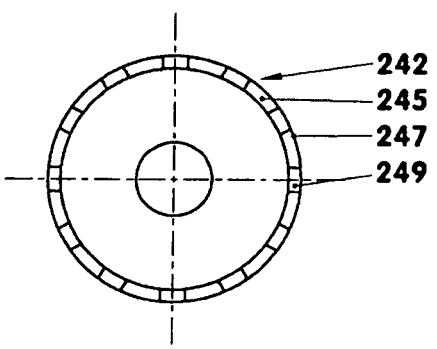
FIG. 12 shows the end face with a supporting cross.
Figure 13:
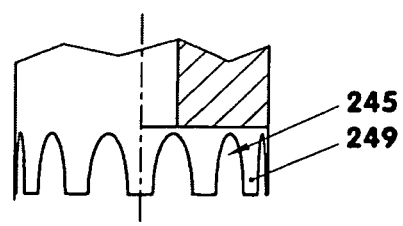
FIG. 13 shows a half-section of FIG. 12.

FIGS. 12 and 13 show in a view and in a half-section the end area of a connecting tube (242) with an outer border (249), which is interrupted by, for example, twelve tubular channels (245). The connecting tube (242) may additionally have an outer annular groove (248).

Figure 14:
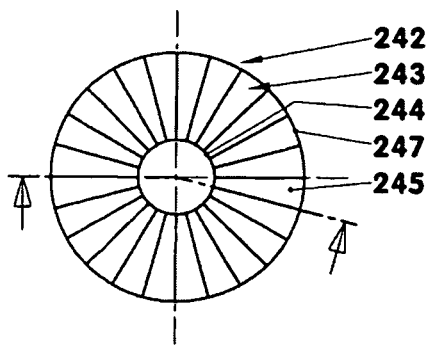
FIG. 14 shows the end face of a displacement tube with 12 tubular channels.
Figure 15:
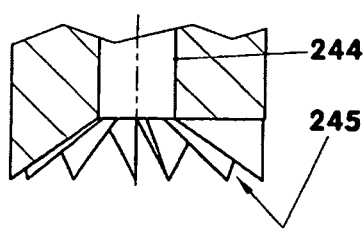
FIG. 15 shows a section through FIG. 14.

In FIGS. 14 and 15, a further variant of the end area of a connecting tube (242) is shown. The end face has a structure comparable to a crown gearing. This ensures a large outlet cross-sectional area of the tubular channels (245).

A pot-shaped cap (290) sits fixedly on the end area of the transfer tube (242) that is facing the container area (221). This cap comprises a, for example cylindrical, elastically deformable wall area (291) and a base area (292), the thickness of which corresponds, for example, to the thickness of the wall area (291) of, for example, 2 millimeters. The base area (292) is surrounded on its inner side by a groove (293), the depth of which is, for example, 90% of the thickness of the base area (292).

The container area (221) has, for example, two groups of locking elements (223, 224), which are set apart from the intermediate base (211) by different distances. The individual locking element (223, 224) is, for example, a triangular element protruding non-radially from the inner wall of the container area (221).

Furthermore, two at least approximately radially arranged slide recesses (228) are arranged in this area (221). At least approximately means here that the center line of the bore can enclose with a radial line an angle of up to 45 degrees. During the manufacture of the container adapter (200), the transfer tube (242) is supported, for example, by means of slides which are guided through these slide recesses (228). It is optionally possible to dispense with a slide recess (228). In the illustration of FIGS. 1 and 2, the slide recesses (228) are covered by a valve hose (229).

The cylinder-piston unit (254) is arranged in the container area (221). The outside diameter of said unit is only slightly smaller than the inside diameter of the container area (221).

The cylinder-piston unit (254) has a cylinder, which is formed from a transparent tube (251), for example a glass or plastic tube (COC), and an elastic stopper (257). The stopper (257), cf. FIG. 6, rests on the flange edge (258) of the glass tube (251).

The underside of the stopper (257), protruding into the chamber (255), has a, for example central, for example cylindrical, recess (271), the depth of which corresponds, for example, to 90% of the thickness of the stopper. The base (272) of the recess (271) is bounded on the upper side of the stopper (257) by an annular groove (273) surrounding it. The diameter of the inner boundary of this groove (273) corresponds, for example, to the diameter of the recess (271). The latter is, for example, dimensioned such that, in the illustration of FIGS. 2 and 7, the connecting tube (242) sits in a sealing manner in the recess (271).

Figure 18:
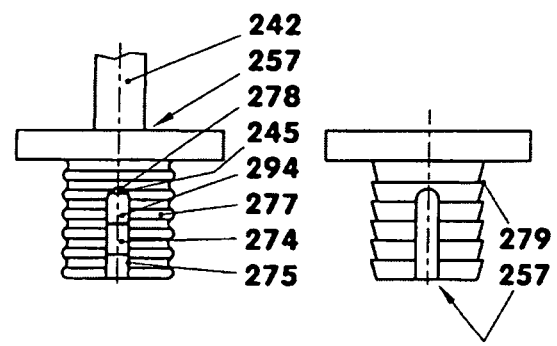
FIG. 18 shows a rubber stopper.

Within the container (250), the recess (271) of the stopper (257), for example a freeze-drying stopper, is connected to the lateral surface (277) of the stopper (257) by means of a channel (275). The depth of the stopper channel (275) is, for example, 60% of the height of the stopper; its width is, for example, one tenth of the maximum diameter of the stopper. The channel base (278) is rounded in the form of a half shell, cf. FIG. 18. The stopper (257) has already been pushed onto the connecting tube (242), cf. FIGS. 2 and 7.

Figure 19:
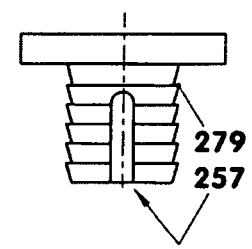
FIG. 19 shows a polyethylene stopper.

The stopper (257) may be produced from polyethylene, for example, instead of from rubber. Such a stopper (257) is shown, for example, in FIG. 19. Its lateral surface (277) has stages (279), which taper frustoconically from top to bottom. For example, with a similarly high coefficient of static friction, the coefficient of sliding friction of polyethylene to polyethylene is less than the coefficient of sliding friction of rubber to rubber.

Figure 20:
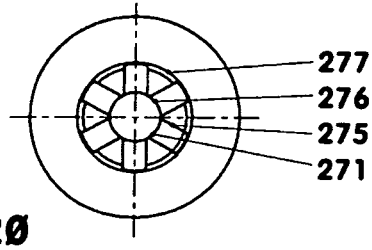
FIG. 20 shows a view of a stopper with six stop channels; and,
FIG. 21 shows a side view of FIG. 20.
Figure 21:
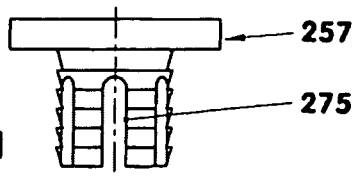

Both types of stopper may have a number of channels (275). FIGS. 20 and 21 show, for example, in a view from below and in a side view a stopper (275) with six regularly arranged channels (275), which, for example, all have the same depth.

The plastic or glass tube (251) is closed at the rear by a movable piston (261). The piston (261) is composed of a piston rod (262), a rear piston pressure plate (264), a front stopper carrier (263) and an elastic piston stopper (267) placed thereover. In order to hold the piston (261) in its rear position when a vacuum has been created in the cylinder interior (252), the piston (261) additionally has two or more locking elements (265), which are, for example, formed integrally on the piston pressure plate (264) and are supported—in an outwardly elastically resilient manner—on the rear edge of the glass or plastic tube (251). An elastic rubber ring (268), which presses the locking elements (265) outward, sits on the rear side of the piston stopper (267).

The piston pressure plate (264) has, toward the tube (251), a cylindrical collar (266), which has the same outside diameter as the container area (221).

In order to prevent triggering, the container adapter (200) is connected to the triggering element (82) of the injector by way of the banderole (90). The banderole (90) is a tamper-evident seal formed as an adhesive label.

The banderole (90) itself is, for example, a strip of paper and/or film which is coated on one side with an adhesive in some areas. It is composed, for example, of three separate strips, which can each be separated from the other by way of a perforation (96) or some other predetermined breaking point. The respectively circumferential perforations (96) lie above the flutes (57) and below the windows (206).

According to FIG. 1, an unwinding banderole (280) is stuck over the container area (221) and the piston (261). The unwinding banderole (280) thereby covers the windows (226) and the locking elements (265) of the piston (261) in a protective manner. In addition, the unwinding film (280) prevents unintentional withdrawal of the container adapter (200) from the housing (10).

During manufacture, the content of the cylinder-piston unit (254) or of the container (250) is, for example, freeze-dried. For this purpose, the stopper (257) is inserted only a few millimeters into the cylinder-piston unit (254) or the container (250), so that the vapor pressure of the frozen injection solution communicates with the vacuum of the freeze-drying chamber. After completion of the freeze-drying, the stopper (275) is pressed in completely. The container content is then closed in a sterile manner. It can then, for example, be stored separately.

The first cylinder-piston unit (100) is, for example, filled with sterile-dispensed water (1) and closed in a sterile, gastight manner with the container adapter (200) provided with the cap (290). This unit can then also be stored in a sterile manner.

The drive unit of the disposable injector (4) is also manufactured separately in a clean room and can be stored separately.

For packing of the single-use injector (4), the sterile second cylinder-piston unit (255) is inserted into the container adapter (200), for example, which closes the first cylinder-piston unit (100). This structural unit, which is sterile on all sides, is then inserted into the drive unit, for example in a clean room, and interlocked.

To be able to use the single-use injector, the active substance (2), for example a lyophilisate, which is stored for example in the cylinder-piston unit (254), must be dissolved in the liquid (1) present in the cylinder (101) of the cylinder-piston unit (100), for example water for injection purposes or physiological saline solution. For this purpose, the liquid (1) must be pumped into the cylinder-piston unit (254).

Figure 7:
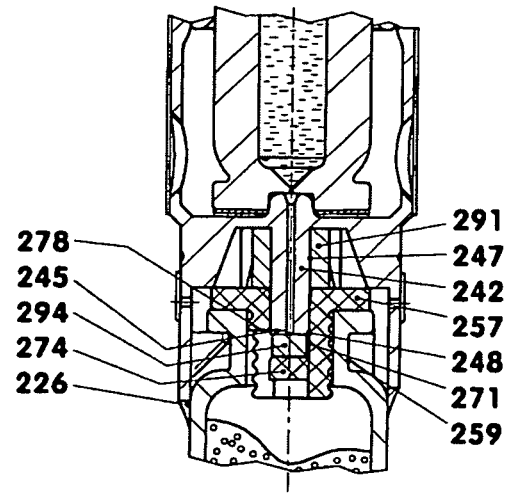
FIG. 7 shows a detail of FIG. 2.

In a first step, the unwinding banderole (280) is removed from the container area (221) and the cylinder-piston unit (254) is pushed into the container adapter (200) in the container pushing-in direction (7), cf. FIGS. 2 and 7. The locking elements (223) are forced outward.

As this happens, the cap (290) comes to rest on the stopper (257). As the cylinder-piston unit (254) is pushed in further, the stopper (257) pushes the cap (290) further upward in the illustration of FIGS. 6 and 7. The transfer tube (242) thereby tears out the cap base (294) and the recess base (274) and forces them into the recess (271). For example, in the case of a structural design of the connecting tube (242) according to FIGS. 12 to 15, the cap base (294) is loaded in the outer area. The recess base (274) bears against the wall surface (276) of the recess (271) and slides along said surface (276) downwardly in the view depicted.

The pushing movement of the cylinder-piston unit (254) is completed when the stopper (257) bears against the stops (225). The notches (259) engage in the locking elements (224). The cap (290) is moved along the transfer tube (242). As the cylinder-piston unit (254) is pushed in, the air thereby displaced escapes through the slide recesses (228) of the container area (221). At the same time, the ingress of contaminated air through the valve hose (229) is prevented.

The transfer tube (242) then protrudes with the lateral-surface-side outlet of the tubular channel (245) and—in the illustrative embodiment—with its annular groove (248) into the container interior (252). The annular groove (248) lies in FIGS. 2 and 7 below the channel base (278) of the stopper channel (275). The transfer tube (242) seals off the container interior (252) in a sterile manner. The cap base (249)—its cross section in a plan view in the direction of movement is, for example, slightly smaller than the cross section of the recess base (274)—rests on the recess base (274), which engages with a force fit in the recess (271). The distance of the channel base (278) from the end face of the stopper (257) protruding into the cylinder-piston unit (254) is consequently greater than the sum of the heights of the recess base (274) and the cap base (294) as well as the diameter of the tubular channel (245).

As a result of the penetration of the transfer tube (242) into the cylinder interior (252), the latter communicates with the cylinder interior (110) of the first cylinder-piston unit (100) by way of the connecting tube (242). The vacuum of the cylinder interior (252) draws the liquid out of the cylinder (101) of the cylinder-piston unit (100). Since the covering of the rear of the cylinder (101) is a sterile filter membrane (119), the drawn-in piston (111) can follow the liquid (1) and comes to bear against the cylinder base (108). In the interior (252), the lyophilisate (2) is dissolved in the liquid (1). The dissolving process may be observed through the windows (226).

In a second step, the tear-off banderole (94) is removed as soon as the lyophilisate (2) has dissolved. The flutes (57) of the triggering element (82) thus become visible. Then the injector is positioned in such a way that the cylinder-piston unit (100) lies below the cylinder-piston unit (250). After that, the newly produced solution (3) should be pumped into the cylinder interior (110) through the transfer tube (242). For this purpose, the piston (261) is firstly primed by radially pressing the locking elements (265) in. Owing to the residual vacuum, the piston stopper (267) comes to lie on the surface of the solution (3). The solution (3) is then transferred by pumping to the cylinder interior (110) by applying a slight pressure to the piston (261). The solution (3) pushes the piston (111) ahead of itself. Bubble-free filling of the cylinder interior (110) is checked in transmitted light through the windows (206). Generally, a small portion of the solution (3) is drawn back into the tube (251), so that, moreover, the piston (111) does not bear against the sterile filter membrane (119).

In a third step, cf. FIG. 4, the container adapter (200) is withdrawn with the cylinder-piston unit (254) from the housing (10). Nevertheless, the injector (4) remains secured.

Once the injector (4) has been placed with the cylinder-piston unit (100) onto the injection site, the blocking button (132) must be pressed in a last step, for example by the thumb of the hand holding the injector (4), in order to be able to move the triggering element (82) together with the triggering cap (81). The triggering element (82) can then be moved in the triggering movement direction (6) in the direction of the cylinder-piston unit (100). During this process, the triggering element (82) slides on the outer wall (13) of the housing (10) linearly downward, that is in the direction of the injection site. The bearing surfaces (24) of the pressure rods (21) slip over the edge (85) and, under the force of the spring element (50), snap radially outward into the widening (83) in a priming manner. The pressure rods (21) have bent elastically outward and are then in their actual starting position. The pressure rods (21), which are then no longer deformed, release the piston actuating ram (60), so that the piston slide (76) moves abruptly toward the sterile filter membrane (119) of the cylinder (101) under the action of the spring element (50). The sterile filter membrane (119) is pierced and the piston (111) is moved downward for draining the cylinder (101), cf. FIG. 5. The cylinder (100) is drained.

Figure 10:
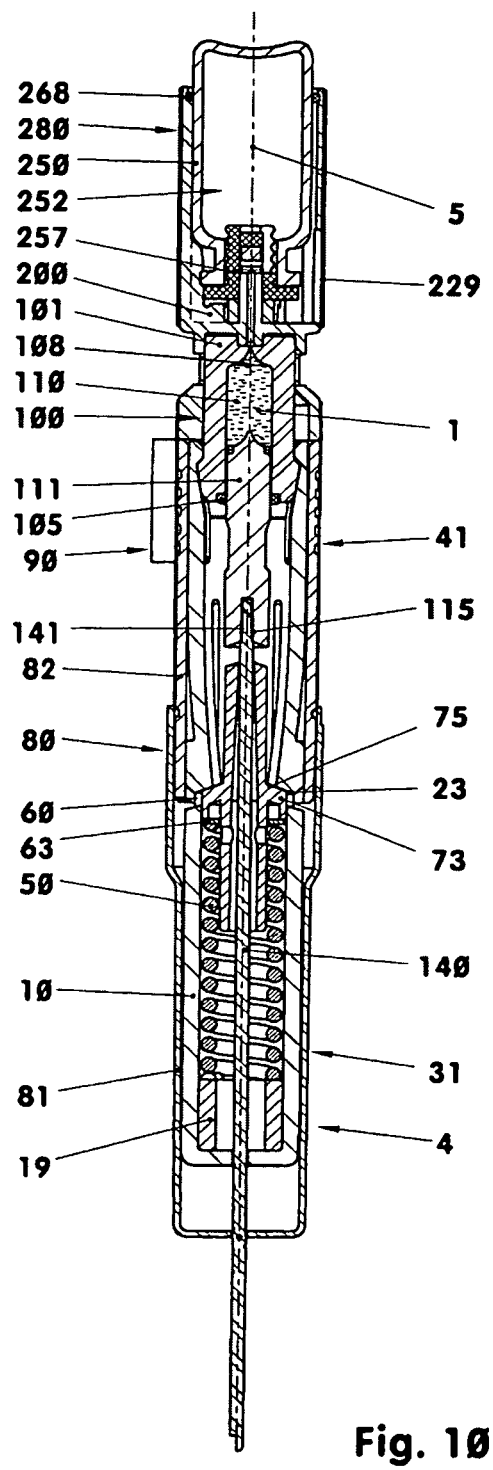
FIG. 10 shows the disposable injector with a pump rod.

FIGS. 8 to 10 show a disposable injector (4) having a twin-chamber system (99), the second chamber (255) of which has a container (250) with a constant container volume.

The disposable injector (4) is constructed in a similar manner to the disposable injector (4) illustrated in FIGS. 1-7. However, the piston (111) has on its rear side a, for example central, frustoconical-envelope-shaped recess (115) into which a pump rod (140) is screwed by means of a conical thread (141), cf. FIG. 10. The piston actuating ram (60) has a, for example central, bore (63), through which the pump rod (140) passes with a high degree of play. The pump rod (140) protruding from the disposable injector (4) can be released from the piston (111) with the expenditure of little force.

A transfer tube (242), the main dimensions of which correspond for example to the main dimensions of the transfer tube (242) described in relation to the first illustrative embodiment, is integrated in the container adapter (200). The end face (243) protruding in the direction of the container receptacle (221) is closed. The tubular channel (245), connecting the central bore (244) to the lateral surface (247), is formed as a, for example continuous, transverse bore, the diameter of which corresponds, for example, to the diameter of the longitudinal bore (244), which is formed, for example, as a tapering blind-hole bore. The transverse bore (245) is aligned with two slide recesses (228) in the, for example cylindrical, side wall of the container receptacle (221) that are covered by means of a valve hose (229). These slide recesses (228) are penetrated, for example during the manufacture of the container adapter (200), by two slides which hold the transfer tube (242) and create the transverse bore (245).

Figure 16:
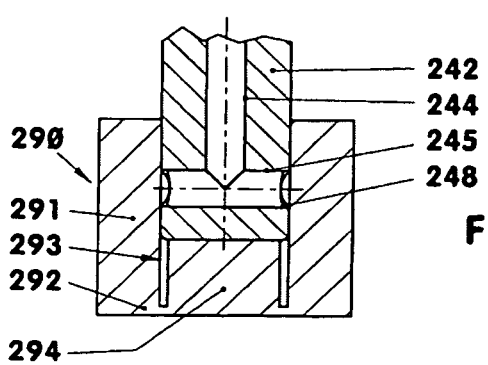
FIG. 16 shows a connecting tube with a transverse bore.

A cap (290), which is for example constructed like the cap (290) described in relation to the first illustrative embodiment, cf. FIG. 16, sits on the transfer tube (242), which is produced like the cylinder (101) and the container adapter (200) from water-vapor-impermeable plastic, for example COC or COP. The connecting tube bore (244) is thus closed in a sterile manner. For transport, this structural unit may, for example, be packed in a double sterile bag.

The cap (290) may, for example, also be of a two-part construction. The cap base (294) then fits in a hose portion that sits on the transfer tube (242).

It is also conceivable to form the flute (293) as a predetermined tearing point or predetermined punching point.

The container (250) is, for example, a glass bottle, or a lyophilisate bottle, with a narrowed neck (259) and a flange edge (258). The flange edge (258) protrudes beyond the neck (259). However, the outside diameter of the flange edge is smaller than the maximum outside diameter of the container. The transition between the neck (259) and the cylindrical outer wall of the container (250) is rounded with a large radius, corresponding, for example, to twice the thickness of the container wall. The container (250) is secured to the container adapter (200) by way of a cap (230) and a tear-off banderole (280).

The opening (253) of the container (250) is closed, for example by a container stopper (257) of rubber, silicone or polyethylene. This may be a further-developed freeze-drying stopper (257). This is constructed, for example, as described in relation to the first-mentioned illustrative embodiment.

The stopper (257) may also be of a two-part construction. For example, the recess base (274) fits in the recess (271), formed for example as a continuous bore, with frictional engagement so as to close it in a sterile manner.

It is also conceivable to form the groove (273) as a predetermined tearing point or predetermined punching point.

In order to be able to use the disposable injector, the active substance (2), for example the lyophilisate, stored in the container (250) must be dissolved in the liquid (1), for example water for injection purposes or physiological saline solution, present in the cylinder (101) of the cylinder-piston unit (100). For this purpose, the liquid (1) should be pumped into the container (250).

In a first step, the tear-off tab (281) is removed from the cap (230), while severing the perforation (282), and the cap (230) is withdrawn from the rear part of the container (250).

Optionally, an elastic sealing ring (217), which closes the joint between the container (250) and the inner wall of the container area (221) in a sterile manner, is located in an annular groove (216) of the container area (221).

In a second step, the container (250) is pushed into the container adapter (200) in the container pushing-in direction (7). In this case, the container (250) slides forward on the inner wall of the container adapter (200) until it bears with the flange edge (258) against the stops (225), cf. FIG. 9. At the same time, the locking rear-engagement means (224) reach around the rear side of the flange edge (258) and thus secure the front position of the container (250). During the forward movement, the container (250) has pressed the folding locking hooks (223) to the side and the locking hooks (224) interlock the container (250) and thus prevent the container (250) from being pulled out. The transfer tube (242) thereby separates the cap base (294) from the rest of the cap (290) and separates the recess base (274) from the rest of the stopper (257) and moves both bases (274, 294) into the recess (271). Owing to the frictional engagement of the recess base (274) in the recess (271), the position of the two parts (274, 294) does not change any longer once the container (250) has been pushed in. The recess base (274) hangs in the recess (271) and carries the, for example likewise frictionally engaged, cap base (294). The wall area (291) of the cap (290) is moved upward in the illustration of FIGS. 9 and 10.

The transverse bore (245) points into the stopper channel (275), so that the cylinder interior (110) and the container interior (252) communicate by way of the transverse bore (245) and the bore (244) of the transfer tube (242). If the connecting tube (242) is turned with respect to the stopper (257) about the central axis (5), the annular groove (248) ensures the communication of the container interior (252) with the cylinder interior (110).

Figure 17:
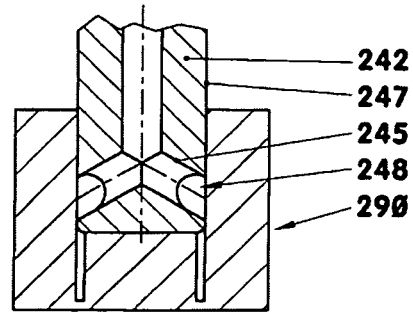
FIG. 17 shows a connecting tube with oblique bores.

FIG. 17 shows a further structural design of the connecting tube (242). The tubular channels (245) are obliquely arranged. With such a structural design, dead volumes during transfer-pumping can be minimized.

The excess pressure produced when the container (250) is pushed into the container area (221) escapes by way of the slide recesses (228) with, for example, partial raising of the valve hose (229). The slide recesses (228) and the valve hose (229) thus have the function of a pressure relief valve.

In a third step, the piston (111) is pushed into the cylinder (101) by means of the pump rod (140) and the liquid (1) is conveyed into the container interior (252), which is now under slight excess pressure. For this purpose, the pump rod (140) is in general held carefully between the index finger and the thumb of the operating hand.

The lyophilisate (2) is dissolved in the liquid (1). The dissolving process can be visually monitored, since the container (250) protruding from the container adapter (200) is transparent.

In a fourth step, the newly produced solution (3) is pumped back into the cylinder interior (110). For this purpose, the injector is held in such a way that the opening (253) of the container (250) points in the direction of gravity. The piston (111) is drawn into a rear position by the pump rod (140). Bubble-free filling is checked through the windows (206), cf. FIG. 10.

In a fifth step, to prime the disposable injector (4), the tear-off banderole (94) is separated all the way round from the main part (92) and from the adapter part (93) with the aid of the tear-off tab (95). The flutes (57) of the triggering element (82) become visible. The container adapter (200), including the container (250), is then pulled off from the cylinder (101), for example downward.

In a last step, the single-use injector (4) is placed onto the injection site and the sleeve-like triggering element (82) is pushed downward in the triggering movement direction (6)—in the direction of the injection site. The pressure rods (21) bend elastically outward into their actual starting position. The cams (22) thereby slip outward over the edge (85) into the widening (83). The pressure rods (21), which are then no longer deformed, release the piston actuating ram (60), so that the piston (111) moves abruptly downward, under the action of the spring element (50), for draining the cylinder (101). During the forward movement of the piston (111), the friction of the piston is reduced for a time, since the rearward sealing element does not bear against it in a slowing manner as it passes the narrowed piston area.

The transfer tube (242) may optionally have on its lateral surface (248), for example, a flattening to fix the position of the stopper (257) in relation to the transfer tube (242). An annular groove (248) is then not required.

The tubular channel (245) and/or the stopper channel (275) may be configured as a radial bore. For example, the lateral surface (247) of the connecting tube (242) or the inner surface of the recess (271) has an annular groove.

The structural designs of the connecting tube (242) and the stopper (257) mentioned in relation to the illustrative embodiment of FIGS. 1-7 may also be used in the case of the illustrative embodiment described in FIGS. 8-10. It is similarly conceivable to use the structural designs mentioned in relation to the illustrative embodiment of FIGS. 8-10 in the illustrative embodiment of FIGS. 1-7.

In all the illustrative embodiments, either the first chamber (105) or the second chamber (255) may receive the active substance (2). The other chamber respectively (255; 105) then receives the solvent (1).

Further combinations of the illustrative embodiments described are also conceivable.

List of Reference Signs 1 water for injection purposes, solvent
2 lyophilisate, active substance, medicament
3 injection solution
4 disposable injector, single-use injector
5 center line of the injector, longitudinal direction
6 triggering movement direction of (82), downward movement directional arrow
7 container pushing-in direction
10 housing, one-part
13 outer surface, cylindrical, outer wall
19 spacer sleeve
21 pressure rods, support rods
22 cams
23 supporting surface
24 bearing surface
28 flexural beam
31 lateral area, lateral portion
33 apertures
39 base
41 fixing area for the cylinder-piston unit
42 spring hook
43 rear-engagement means
50 spring element, helical compression spring, spring energy store
57 flutes of (82)
59 inner wall of (82)
60 piston actuating ram
62 guide pin
63 central bore
73 ram plate
75 collar surface, conical
76 piston slide
80 triggering unit
81 triggering cap
82 triggering element, triggering sleeve
83 widening
84 return flank
85 edge, sharp-edged
90 tamper-evident seal, banderole, security element, adhesive label
92 edge part, rear; label part
93 edge part, front; label part
94 tear-off banderole
95 tear-off tab
96 perforations, predetermined breaking points
99 twin-chamber system
100 cylinder-piston unit, first, injector-side
101 cylinder, injector-side
102 locking ring
103 end face
104 adhesive ring
105 chamber, first; injection-side chamber
106 bore, nozzle
107 recess in the end face
108 cylinder base
110 cylinder interior
111 piston
112 annular groove
114 sealing ring, seal
115 recess in (111)
119 sterile filter membrane
132 blocking button
140 pump rod
141 conical thread
200 container adapter
201 adapter area
204 shoulder, annular
206 window, on both sides
211 intermediate base
213 elevation
216 annular groove
217 sealing ring
221 container area, container receptacle
223 locking elements, folding locking hooks
224 locking elements, locking rear-engagement means
225 stops
226 windows
228 slide recesses
229 valve hose
230 cap 242 transfer tube, connecting tube
243 end face
244 bore, transfer tube bore, longitudinal bore
245 channel, tubular channel; transverse bore
247 lateral surface
248 groove, circumferential; annular groove
249 border
250 container
251 tube, glass tube, plastic tube
252 cylinder interior, container interior
253 opening
254 cylinder-piston unit
255 chamber, second
257 stopper, elastic, rubber stopper
258 flange edge
259 notches, neck
261 piston
262 piston rod
263 stopper carrier
264 piston pressure plate
265 locking elements
266 collar
267 plunger stopper
268 rubber ring, elastomer ring
271 recess, central recess
272 base of (271)
273 groove, predetermined tearing point, predetermined punching point
274 recess base
275 channel, stopper channel
276 wall surface
277 lateral surface
278 channel base
279 stages
280 unwinding banderole, tear-off banderole
281 tear-off tab
282 perforation
290 cap
291 wall area
292 base area
293 groove, predetermined tearing point, predetermined punching point
294 cap base

What is claimed is:

1. In combination with a device, comprising
a disposable injector (4) having a sterile and gastight cylinder-piston unit (100), which has a first chamber (105),
a container adapter (200) mounted on the disposable injector (4), and
a container (250) releasably fitted on the container adapter (200) and having a second chamber (255), or a cylinder-piston unit (254) with a second chamber (255), the cylinder-piston unit (254) releasably fitted on the container adapter (200), the second chamber (255) is at least temporarily closed in a sterile and gastight manner by means of a stopper (257), the container adapter (200) comprises a connecting tube (242) having a lateral surface (247), the connecting tube (242) having a longitudinal bore (244) initially closed by means of a cap (290) and having at least one tubular channel (245) connecting the longitudinal bore (244) to the lateral surface (247), the improvement which comprises:
the cap (290) includes a detachable cap base (294), the cap base (294) is initially surrounded on its inner side by a groove (293);
the stopper (257) having a lateral surface (277), the stopper (257) at the top thereof has on its underside oriented toward the second chamber (255) a central recess (271), the stopper at the top thereof includes a recess base (274) that initially lies above and aligned with the central recess (271), the recess base (274) is initially bounded on the upper side of the top of the stopper (257) by a surrounding annular groove (273), the stopper (257) below the top thereof has therein at least one stopper channel (275) connecting the lateral surface (277) of the stopper (257) to the central recess (271), the at least one stopper channel (275) having a channel base (278) nearest the top of the stopper (257),
the central recess (271) is sized to receive and to hold the cap base (294) and recess base (274), both the cap base (294) and the recess base (274) are moved within the central recess (271) by means of the connecting tube (242) when the container (250) or the cylinder-piston unit (254) is pushed in or activated and the cap base (294) and the recess base (274) are held by the stopper (257) in predetermined position after activation,
after the container (250) has been pushed in or activated, the connecting tube (242) connects the interior (110) of the cylinder-piston unit (100) to the interior (252) of the container (250) or the cylinder-piston unit (254) by way of the at least one stopper channel (275) and the tubular channel (245).

2. The device as claimed in claim 1, wherein the cross section of the recess base (274) corresponds to the cross section of the recess (271).

3. The device as claimed in claim 2, wherein the cross section of the cap base (294) is smaller than the cross section of the recess base (274).

4. The device as claimed in claim 1, when the container (250) or the cylinder-piston unit (254) is pushed in or activated the recess base (274) is frictionally engaged with the central recess (271).

5. The device as claimed in claim 4, when the container (250) or the cylinder-piston unit (254) is pushed in or activated the cap base (294) is frictionally engaged with the central recess (271).

6. The device as claimed in claim 1, wherein firstly one chamber (105; 255) is at least partially filled with an active substance (2) and the other chamber respectively (255; 105) is at least partially filled with a solvent (1).

7. The device as claimed in claim 1, wherein the distance of the channel base (278) from the container (250) or cylinder piston unit (254) -side end face of the stopper (257) is greater than the sums of the lengths of the cap base (294) and the recess base (274) as well as the diameter or the depth of the tubular channel (245).

8. The device as claimed in claim 1, wherein the tubular channel (245) is at least approximately radially oriented.

9. The device as claimed in claim 1, wherein the tubular channel (245) is arranged at the end face of the connecting tube (242).

10. The device as claimed in claim 1, wherein the lateral surface (247) of the connecting tube (242) has a circumferential annular groove (248).

11. The device as claimed in claim 1, wherein the cap (290) has an elastically deformable wall area (291) surrounding the detachable cap base (294).

12. The device as claimed in claim 1, when the container (250) or the cylinder-piston unit (254) is pushed in or activated the connecting tube (242) sits in a sealing manner in the recess (271).

13. The device as claimed in claim 1, wherein the channel base (278) is rounded in the form of a half shell.

14. The device as claimed in claim 1, wherein the lateral surface (277) of the stopper (257) has a plurality of stages (279) each tapering frustoconically from the top to the bottom.

* * * * *